(12) United States Patent
Marterstock

(10) Patent No.: US 9,415,201 B2
(45) Date of Patent: Aug. 16, 2016

(54) MEDICAL DEVICE COMPRISING A SOCKET UNIT FOR CONNECTING A PLUG UNIT OF A DEVICE FOR PROVIDING MEDICAL FLUIDS

(71) Applicant: Fresenius Medical Care Deutschland GmbH, Bad Homburg v.d.H. (DE)

(72) Inventor: Stefan Konrad Marterstock, Eussenheim-Hundsbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 226 days.

(21) Appl. No.: 14/166,566

(22) Filed: Jan. 28, 2014

(65) Prior Publication Data

US 2014/0213962 A1  Jul. 31, 2014

Related U.S. Application Data

(60) Provisional application No. 61/757,786, filed on Jan. 29, 2013.

(30) Foreign Application Priority Data

Jan. 29, 2013 (DE) .......................... 10 2013 001 438

(51) Int. Cl.
*A61M 1/00* (2006.01)
*A61M 39/12* (2006.01)
*A61M 39/10* (2006.01)
*A61M 39/14* (2006.01)
*A61M 1/16* (2006.01)
*A61M 1/28* (2006.01)

(52) U.S. Cl.
CPC .................. *A61M 39/12* (2013.01); *A61M 1/16* (2013.01); *A61M 39/10* (2013.01); *A61M 39/105* (2013.01); *A61M 39/14* (2013.01); *A61M 1/28* (2013.01); *A61M 2039/1005* (2013.01); *A61M 2205/14* (2013.01); *A61M 2209/00* (2013.01)

(58) Field of Classification Search
CPC ........ A61M 1/301; A61M 39/12; A61M 1/28
USPC .................................................. 604/152, 29
See application file for complete search history.

(56) References Cited

U.S. PATENT DOCUMENTS

| | | |
|---|---|---|
| 2007/0066940 A1 | 3/2007 | Karunaratne et al. |
| 2007/0179473 A1 | 8/2007 | Masters et al. |
| 2010/0270792 A1 | 10/2010 | Lauer |

FOREIGN PATENT DOCUMENTS

| | | |
|---|---|---|
| DE | 10 2009 024 575 A1 | 12/2010 |
| EP | 0575970 A2 | 12/1993 |

*Primary Examiner* — Edelmira Bosques
(74) *Attorney, Agent, or Firm* — Kenyon & Kenyon LLP

(57) ABSTRACT

A medical device comprising a socket unit for connecting a plug unit and an automated connection of the plug unit to the socket unit via a connecting mechanism. The connecting mechanism has a drive unit that has at least one movable drive body that carries out a translational and/or rotational movement and a position detection mechanism for detecting the linear position and/or the angular position of the drive body. The position detection mechanism includes at least two magnet elements, and at least one sensor element. The linear position and/or angular position of the drive body is determined with an evaluation unit on the basis of the magnetic field generated by the at least two magnet elements and detected by the at least one sensor element.

16 Claims, 10 Drawing Sheets

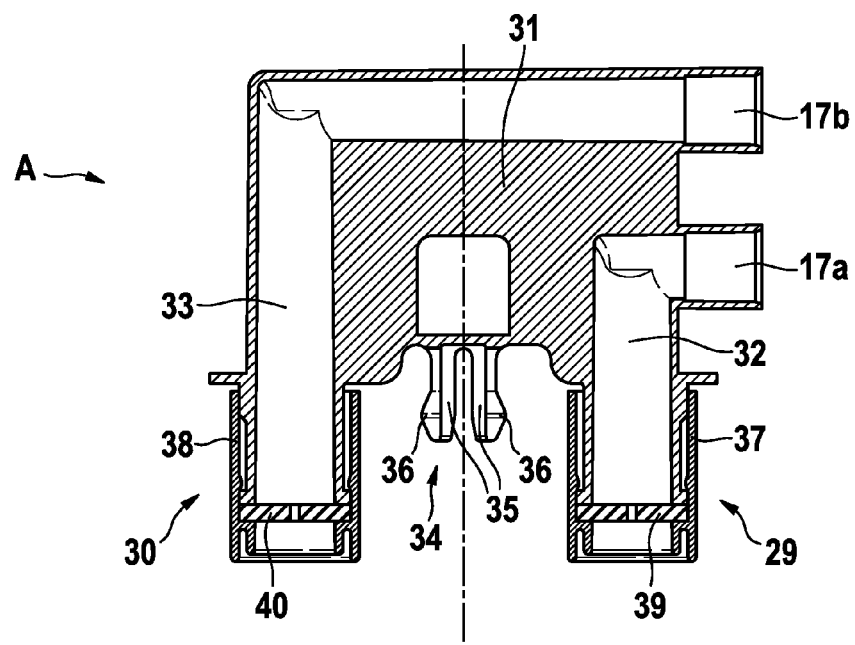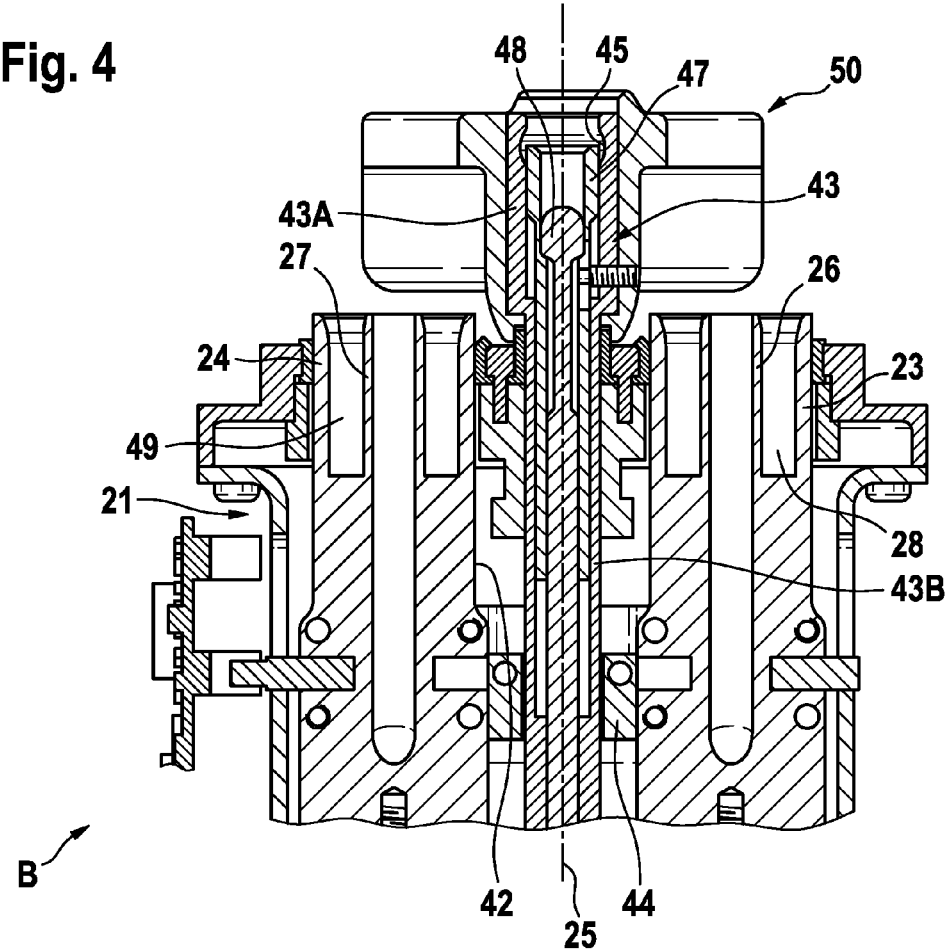
Fig. 4

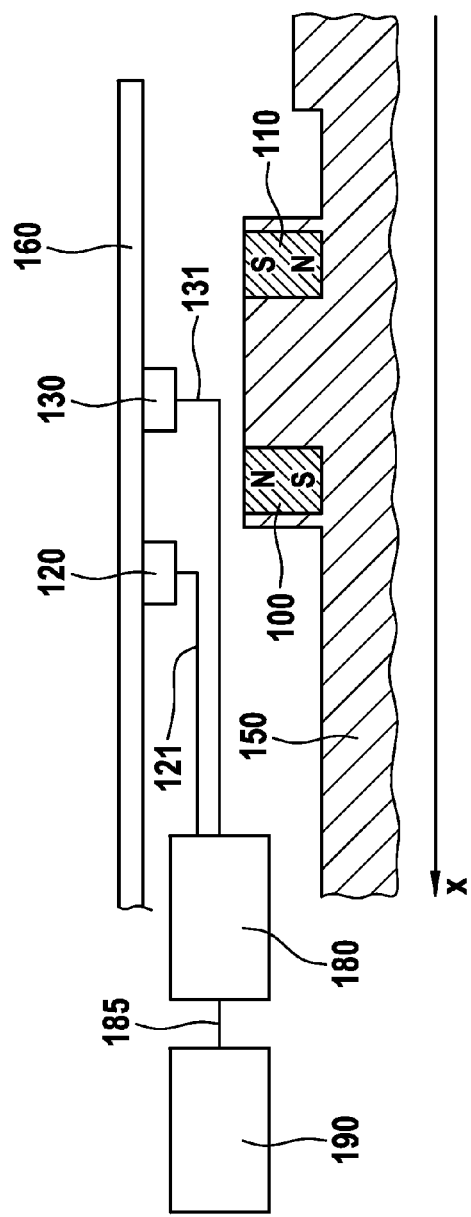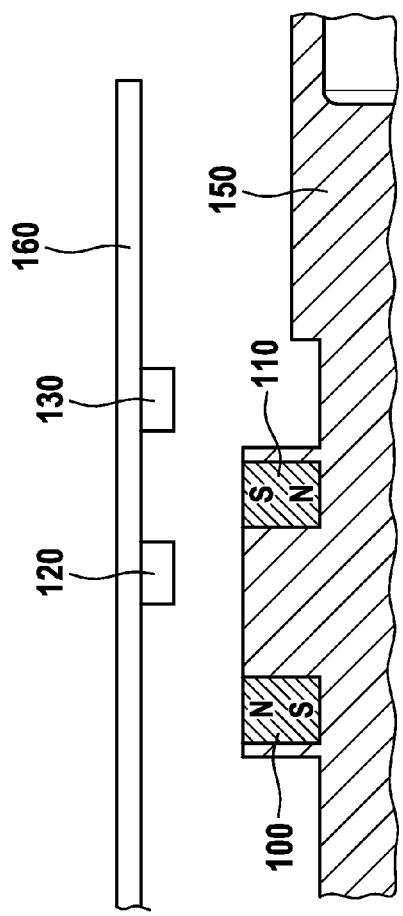

MEDICAL DEVICE COMPRISING A SOCKET UNIT FOR CONNECTING A PLUG UNIT OF A DEVICE FOR PROVIDING MEDICAL FLUIDS

CROSS REFERENCE TO RELATED APPLICATIONS

The present application claims priority to U.S. Provisional Application Ser. No. 61/757,786, filed on Jan. 29, 2013, and claims priority to Application No. DE 10 2013 001 438.7, filed in the Federal Republic of Germany on Jan. 29, 2013, each of which is expressly incorporated herein in its entirety by reference thereto.

FIELD OF INVENTION

The present invention relates to a medical device comprising a socket unit for connecting a plug unit of a device for providing medical fluids, wherein the medical device is in particular an extra-corporal blood treatment device, for example an extra-corporal dialysis device or a device for peritoneal dialysis, and the medical fluid is in particular a dialysis fluid.

BACKGROUND INFORMATION

For connecting external components to medical-technical systems, different connectors are known. The access to the medical-technical systems generally takes place by means of plugs that are plugged into matching sockets of the medical-technical systems. In this respect, the medical-technical systems, hereinafter generally designated as medical devices, comprise a corresponding socket unit, whereas the external components have a plug unit.

For treating kidney patients, blood treatment devices are used, which include in particular the known extra-corporal dialysis devices or devices for peritoneal dialysis. For cleansing the blood of the patient, providing medical treatment fluids is required, which can be provided in fluid reservoirs that are connected to the blood treatment devices. Connecting the fluid reservoir to the blood treatment devices is carried out with a plug unit that is plugged into a socket unit of the blood treatment device.

A device for providing a treatment fluid is known from EP 0 575 970 A2. The known device for providing a dialysis fluid comprises a bag for receiving the fluid, to which bag a tube line is connected that is connected at its free end to a plug. The dialyzer has a socket into which the plug is plugged. With the plug and the socket, two flow connection can be established so as to be able to feed fresh dialysis fluid from the bag into the dialysis device and to feed used dialysis fluid back into the bag.

Connecting the device for providing medical fluids to the blood treatment device shall be as simple and secure as possible for the medical staff. For disinfection, it should be possible to rinse the socket unit with a rinsing fluid.

The socket unit of the blood treatment device known from EP 0 575 970 A2 comprises a system for detecting the position of the plug unit in the socket unit, which system comprises a reed contact in the socket unit and a magnet in the plug unit.

SUMMARY

It is an object of the present invention to make the supply of medical fluids to medical devices, in particular to blood treatment devices, for example extra-corporal dialysis devices or devices for peritoneal dialysis, simpler for the medical staff, and to increase the safety of the treatment.

It is in particular an object of the present invention to detect an operating state of the medical device in a simple and reliable manner, and in particular, to provide a simple and secure solution for the position determination of a movable component of the socket unit of the medical device.

The medical device according to the present invention has a socket unit, while the device for providing medical fluids has a plug unit.

The socket unit and the plug unit are characterized in that with both units a flow connection can established in a simple and secure manner between the medical device on the one hand, and the device for providing medical fluids on the other.

For establishing the flow connection, the socket unit has at least one connecting piece while the plug unit has at least one connector so that a fluid-tight connection can be established when the connector is connected to the connecting piece. It is not an essential component how the connecting piece and the connector are designed. The connecting piece and the connector, for their parts, can also be plug and socket, respectively.

The medical device provides an automated connection of the plug unit to the socket unit by means of a connecting mechanism for establishing a connection between the at least one connecting piece and the at least one connector.

The connecting mechanism comprises a drive unit that has at least one movable drive body that carries out a translational and/or rotational movement so as to carry out the connection of socket unit and plug unit.

Moreover, the connecting mechanism comprises a position detection mechanism for detecting the linear position and/or the angular position of the drive body. Detecting the position and/or the angular position enables monitoring the operating state or controlling the medical device.

A preferred embodiment of the present invention provides that the drive unit of the connecting mechanism comprises a drive body that has means for detachably connecting the plug unit to the socket unit. The means for detachably connecting the plug unit to the socket unit preferably have a receptacle for plugging in an attachment part of the plug unit.

A further preferred embodiment provides that the at least one connecting piece of the socket unit is concentrically enclosed by a connecting part thereby forming a rinsing chamber, whereby the socket unit has a closure body with at least one closure piece for closing the at least one rinsing chamber.

In this embodiment, the closure body is provided on a drive body that is pivotable about a pivot axis. The closure piece is arranged on the closure body and is spaced apart from the pivot axis, wherein the closure body can be pivoted between a first and a second pivot position.

In the first pivot position, the at least one closure piece and the at least one connecting part or connecting piece lie on a common axis so that by a relative movement of plug unit and socket unit, a connection between closure piece and connecting part can be established for closing the rinsing chamber. In this connection, a relative movement of closure piece and connecting part is to be understood as a movement of a displaceable closure piece on a stationary connecting part or as a movement of a displaceable connecting part on a stationary closure piece.

In the second pivot position, the at least one closure piece and the at least connecting part or connecting piece are arranged offset to one another so that when plugging the plug unit into the socket unit, a connection between the at least one connector of the plug unit and the at least one connecting piece of the socket unit can be established.

Depending on the angular position of the pivotable drive body, the actions required for connecting the plug unit and the socket unit or for rinsing can be controlled or monitored.

It is not an essential component for the present invention how the drive body is configured. The drive body can be any longitudinally displaceable or pivotable component of the connecting mechanism.

The position detection mechanism for the drive body of the connecting mechanism is characterized by at least two magnet elements that are arranged spaced apart from each other and generate a magnetic field, and at least one sensor element that detects the magnetic field of the magnet elements, wherein the at least two magnet elements are arranged on the drive body and the at least one sensor element is arranged stationarily, or the at least two magnet elements are arranged stationarily and the at least one sensor elements is arranged on the drive body. Here, the evaluation unit is configured such that the linear position and/or the angular position of the drive body is determined based on the magnetic field generated by the at least two magnet elements and detected by the at least one sensor element. The two sensor elements allow a clear detection of the linear position and/or angular position over a wide movement range of the drive body.

In one preferred embodiment, a first magnet element and a second magnet element that are spaced apart from each other with opposite polarity, and a first sensor element and a second sensor element that are spaced apart from each are provided, wherein the evaluation unit is configured such that based on the magnetic field detected by the first sensor element, two possible linear positions and/or angular positions of the drive body are determined, and based on the magnetic field detected by the second sensor element, it is determined whether the linear position and/or angular position determined with the first sensor element is the first or the second linear position and/or angular position of the two possible positions and/or angular positions. The differentiation between the two possible linear positions and/or angular positions can take place based on the sign of the magnetic field detected by the second sensor element.

An alternative embodiment provides a limitation of the translational and/or rotational movement of the drive body through one or a plurality of stop elements to a movement range in which a clear determination of the position and/or the angular position is possible.

In a further alternative embodiment, the position detection mechanism comprises a first magnet element and a second magnet element that are spaced apart from each other with opposite polarity, wherein for a clear determination of the position and/or angular position, only one sensor element is provided. For this, the evaluation unit is configured such that based on the magnetic field detected by the sensor element, two possible linear positions and/or angular positions of the drive body are determined, and that the evaluation unit is configured such that the gradient of the change of the magnetic field detected by the sensor element is determined in the case of a change of the linear position and/or angular position of the drive body. On the basis of the sign of the gradient of the change it is possible to clearly differentiate between the two positions and/or angular positions.

The evaluation unit can generate a first control signal when the position detection mechanism detects a first advanced position of the drive body in which the at least one connector and the at least one connecting piece are disconnected, and can generate a second control signal when the position detection mechanism detects a second retracted position when the at least one connector is connected to the at least one connecting piece. The position detection mechanism can also generate control signals when a first pivot position and a second pivot position of the drive body are detected.

The magnet element is preferably a permanent magnet. However, it can also be an electromagnet. The sensor element is preferably a Hall sensor or a magnetoresistive sensor, or can also be any other sensor for detecting a magnetic field.

The medical device can be a blood treatment device, in particular an extra-corporal dialysis device or a device for peritoneal dialysis.

BRIEF DESCRIPTION OF THE DRAWINGS

Exemplary embodiments are explained in more detail hereinafter with reference to the Figures, in which:

FIG. 4 shows the plug unit and the socket unit of FIG. 2 in a sectional illustration, wherein the socket unit is prepared for connecting the plug unit.

FIG. 9 shows a simplified illustration of a first embodiment of the position detection device with two magnet elements and two sensor elements for detecting the linear position of a translational drive body, wherein the drive body is in a first position.

FIG. 10 shows a position detection mechanism of FIG. 9, wherein the drive body is in a second position.

DETAILED DESCRIPTION

Hereinafter, first the medical device including the socket unit is described in detail with reference to FIGS. 1 to 7. Subsequently, the position detection mechanism of the connecting mechanism of the medical device is described in detail with reference to FIGS. 8 to 12.

Figure 1:
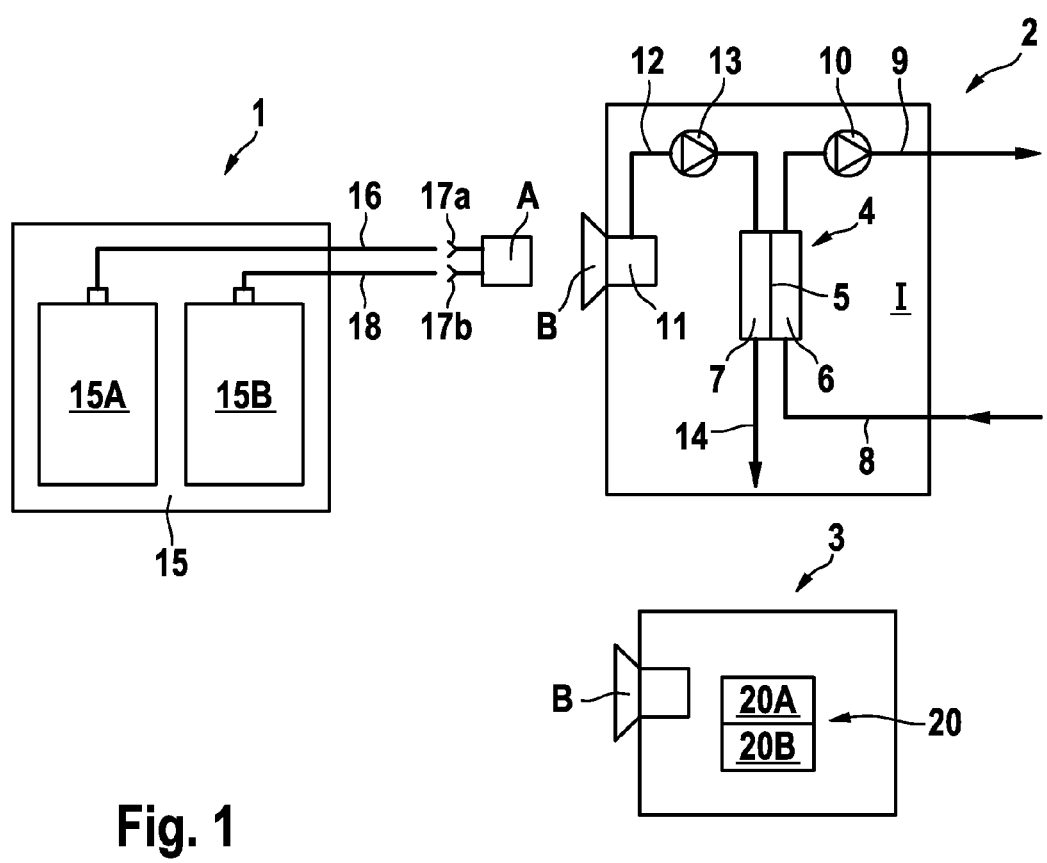
FIG. 1 shows a device for providing a medical fluid, in particular a dialysis fluid, together with a blood treatment device and a device for filling the device for providing a dialysis fluid, in a simplified schematic illustration.

FIG. 1 shows in a simplified schematic illustration a device 1 for providing a medical fluid, in particular a dialysis fluid, together with a blood treatment device 2 and a device 3 for filling the device for providing a dialysis fluid. The blood treatment device 2 as an example for the medical device according to the present invention can be an extra-corporal dialysis device or a device for peritoneal dialysis. In the present exemplary embodiment, the blood treatment device 2 is a dialysis device comprising a dialyzer 4 that is subdivided by a semipermeable membrane into a blood chamber 6 and a dialysis fluid chamber 7. From the patient, a blood supply line 8 runs to the blood chamber 8 of the dialyzer 4 while a blood recirculation line 9, into which a blood pump 10 is integrated, runs from the blood chamber 6 to the patient. The blood supply line and recirculation lines 8, 9 form together with the blood chamber 6 the extra-corporal blood circulation I of the dialysis device 2.

The fresh dialysis fluid is fed from a dialysis fluid reservoir 11 via a dialysis fluid supply line 12, into which a dialysis fluid pump 13 is integrated, to the dialysis fluid chamber 7 of the dialyzer 4, while used dialysis fluid flows out of the dialysis fluid chamber via a dialysis fluid discharge line 14.

The device 1, which in the present exemplary embodiment has two bags or containers 15A and 15B, serves for providing fresh dialysis fluid. Both bags or containers 15A, 15B form a unit 15, wherein the bag 15A is filled prior to the dialysis treatment with fresh dialysis fluid and the bag 15B is empty.

From the dialysis fluid bag 15A, a feed line 16 runs to the one connection 17a of a plug unit A, while from the other connection 17B of the plug unit A, a drain line 18 runs to the empty bag 15B.

For providing dialysis fluid, the plug unit A is connected prior to the treatment to a socket unit B that is provided on the blood treatment device 2 so that fresh dialysis fluid is fed via the feed line 16 to the dialysis fluid reservoir 11 and used dialysis fluid can be discharged via the drain line 18. However, the dialysis fluid can also be fed directly to the dialysis fluid chamber 7 of the dialyzer.

The device 1 for providing dialysis fluid is filled at the device 3 with fresh dialysis fluid. With the device 3 for filling, the device 2 for providing dialysis fluid can also be emptied. A tank 20A serves for receiving fresh dialysis fluid and a tank 20B serves for receiving used dialysis fluid. The required lines and pumps are not shown in the schematic illustration.

The device 3 for filling and emptying the device 1 for providing fresh and receiving used dialysis fluid 1 comprises a socket unit B to which the plug unit A of the device 1 for providing dialysis fluid is connected. The socket unit B of the blood treatment device 2 and the socket unit B of the device 3 for filling or emptying can be designed identically or differently. In the present exemplary embodiment, the socket units B are designed identically. Both socket units B are designed such that with the plug unit A of the device 1 for providing dialysis fluid, a fluid-tight flow connection can be established with both devices 2 and 3 in both directions for fresh and used dialysis fluid.

Hereinafter, the plug unit A of the device 1 for providing dialysis fluid is described in detail together with the socket unit B with reference to FIGS. 2 to 7.

Figure 2:
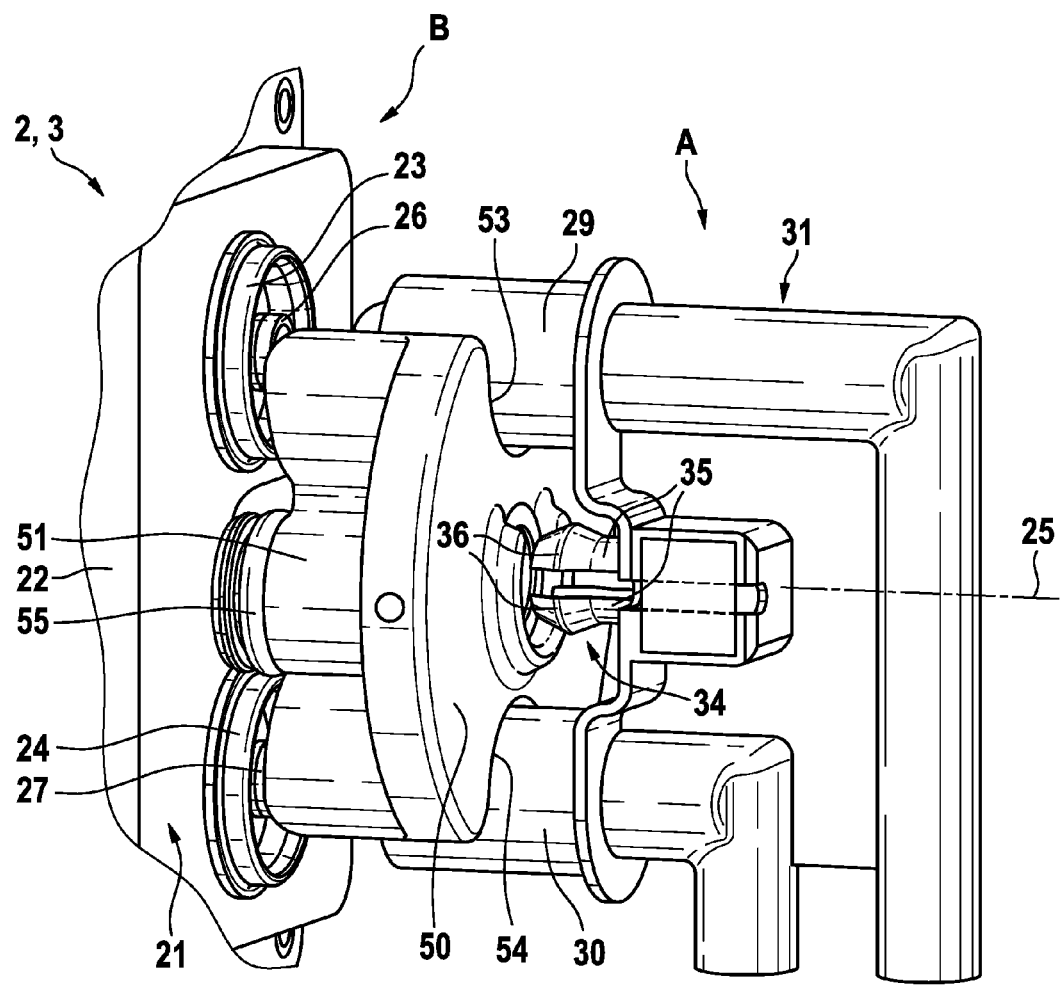
FIG. 2 shows the plug unit of the device for providing a dialysis fluid together with the socket unit of the blood treatment device in a perspective illustration.
Figure 3:
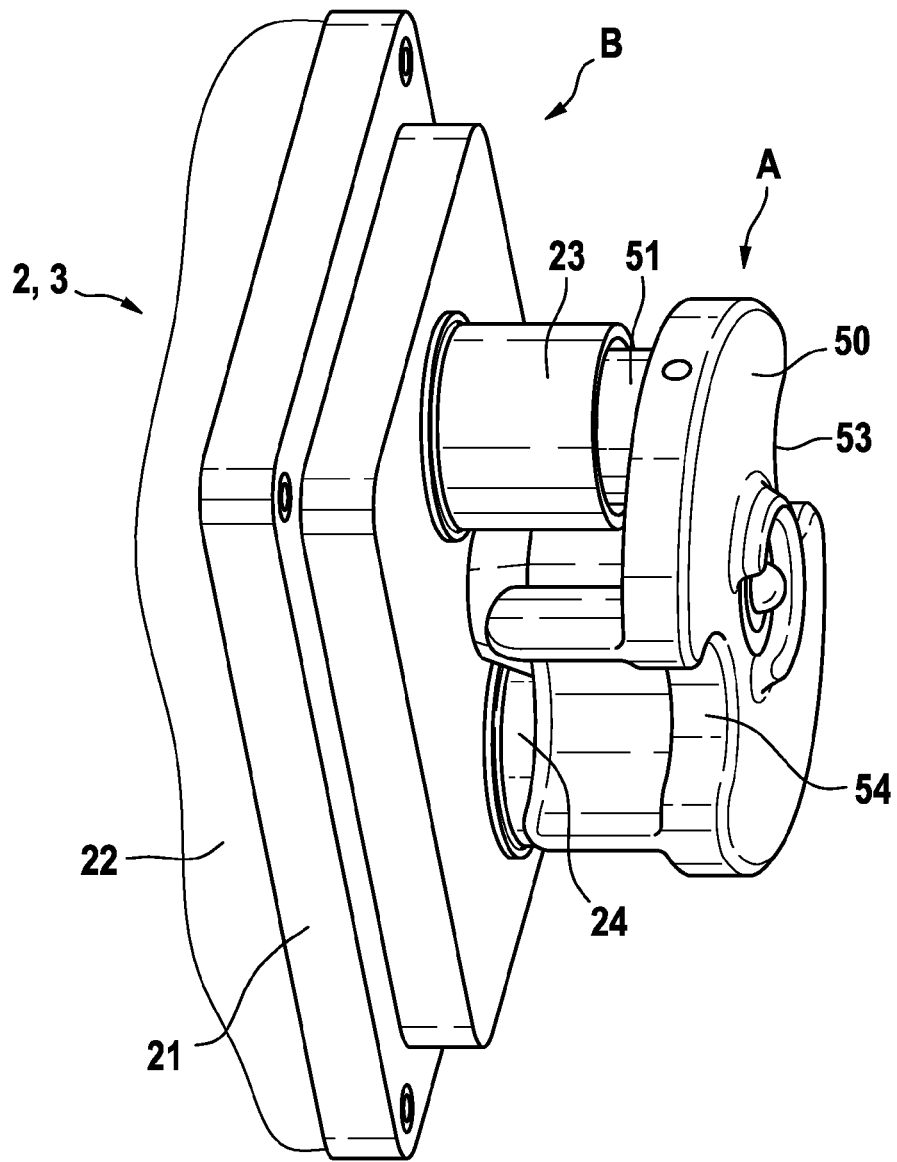
FIG. 3 shows the socket unit of FIG. 2 in a perspective illustration, wherein the socket unit is prepared for a rinsing process.

FIGS. 2 and 3 show the plug unit A and the socket unit B in a perspective illustration while the FIGS. 4 to 7 show the plug and socket units A, B in a sectional illustration.

FIG. 2 shows the socket unit B together with the plug unit A in a perspective illustration. With the plug unit A, the device 1 for providing dialysis fluid can be connected, on the one hand, to the device 3 for filling and emptying and, on the other, to the blood treatment device 2.

The socket unit B has a housing body 21 that is inserted in a housing wall 22 of the blood treatment device 2 or the device 3 for filling. In the housing body 21 of the socket unit B, two cylindrical connecting parts 23, 24 are provided which are arranged in a common plane on both sides of the central axis 25 of the socket unit. The cylindrical connecting parts 23, 24 each enclose a connecting piece 26 and 27, respectively, wherein the connecting piece 26 serves for feeding fresh dialysis fluid and the connecting piece 27 serves for discharging used dialysis fluid (FIGS. 4 to 7).

Figure 7:
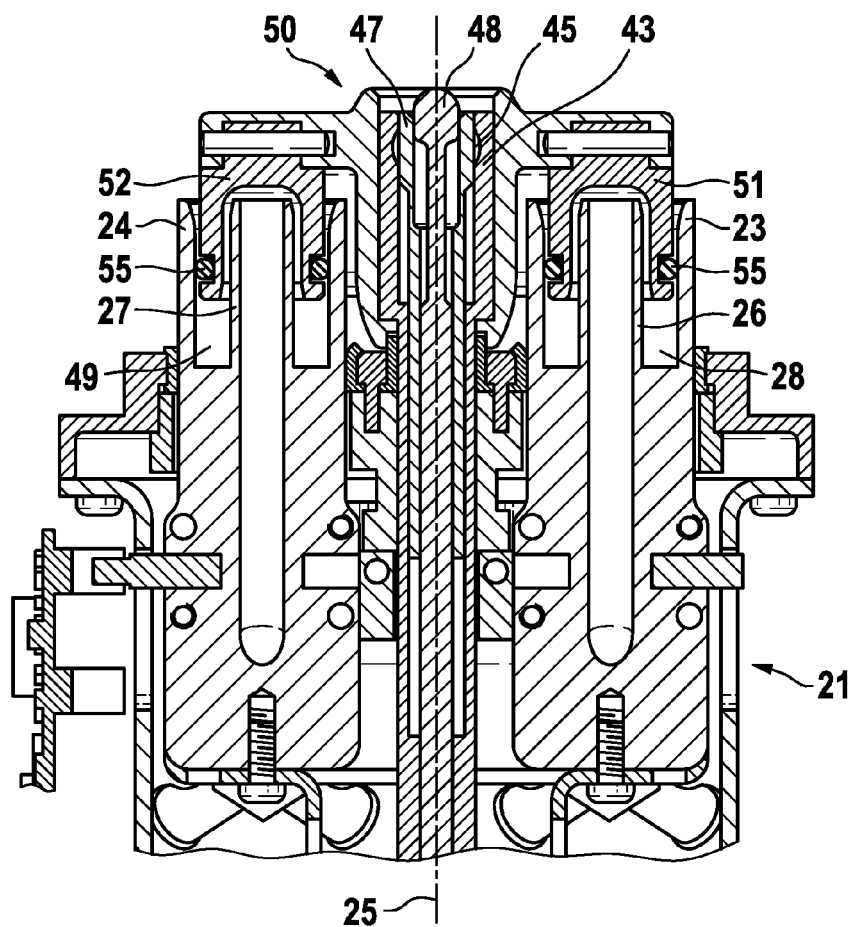
FIG. 7 shows the socket unit of FIG. 2 in a sectional illustration, wherein the socket unit is prepared for a rinsing process.

The two connecting parts 23, 24 each enclose a space that can be closed in a fluid-tight manner. The fluid-tightly closed space forms a rinsing chamber 28, 49 through which a rinsing fluid can be fed which can flow in or out via channels that are not shown in detail (FIG. 7). For rinsing the socket unit B, rinsing fluid flows through the rinsing chambers 28, 49 (described in detail below).

The connecting parts 23, 24 of the socket unit B are guided together with the connecting pieces 26, 27 in a longitudinally displaceable manner in the housing body 21 so that the connecting parts and pieces can be advanced from the housing body or retracted into the housing body. The drive unit for advancing or retracting the connecting parts and pieces is not shown in detail in the Figures. It can be an electromotive or hydraulic drive unit.

The plug unit A (FIGS. 4 to 6) of the device 1 for providing fresh dialysis fluid and receiving used dialysis fluid comprises suitable connectors 29, 30 that are connected to the connecting pieces 26, 27 in a fluid-tight manner. The plug unit A has a plug body 31 that connects the two connectors 29, 30. The plug body 31 has a feed channel 32 that is connected to the one connector 29, and has a drain channel 33 that is connected to the other connector 30. At the connection 17a of the feed channel 32, the feed line 16 is connected, and at the connection 17b of the drain channel 33, the drain line 18 of the device 1 for providing fresh dialysis fluid and/or for receiving used dialysis fluid is connected. Between the two connectors 29, 30 there is an attachment piece 34 by means of which an initially only loose connection can be established between the plug unit A and the socket unit B.

The attachment piece 34 has a plurality of latching elements 35 that are arranged circumferentially distributed and are formed on an end of the attachment piece. At the outer sides of the free ends of the latching elements 35, latching lugs 36 are formed. The connectors 29 and 30 comprise contact protection sleeves 37 and 38 that are attached onto the connectors 29, 30 of the plug body 31 in a latching manner. The connectors 29, 30 are in each case closed by a membrane 39, 40 that is penetrated by the connecting pieces 26, 27 of the socket unit B.

The housing body 21 of the socket unit B has a central recess 42 in which a tubular receptacle 43 is arranged into which the attachment piece 34 of the plug unit A can be inserted. The receptacle 43 is mounted with a bearing 44 to as to be pivotable about the axis 25, which bearing is inserted in the central recess 42 of the housing body 21. The receptacle 43 is pivoted with the drive unit.

The tubular receptacle 43 has a front section 43A extending out of the housing body 21 and a rear section 43B extending into the housing body, wherein the front section 43A has a larger outer and/or inner diameter than the rear section 43B. On the inner side of the front end of the front section 43A of the receptacle 43, circumferentially distributed recesses 45 are provided into which the latching lugs 36 of the latching elements 35 of the attachment piece 34 snap in when the plug unit A is loosely attached onto the socket unit B.

In the tubular receptacle 43, a probing element 47 designed as a tubular body is guided in a longitudinally displaceable manner and is preloaded with a spring (not shown in the Figures), so that when inserting the attachment piece 34 into the receptacle 43, the probing element 47 is pushed back against the spring load.

A pin-shaped body 48 for locking the attachment piece 34 in the receptacle 43 is guided in the tubular probing element 47. The pin-shaped body 48 can be advanced in the longitudinal direction by a drive unit (not shown in the Figures) and can be retracted again so as to release and lock, respectively, the attachment piece 34 in the receptacle 43.

FIG. 4 shows the socket unit B in the position in which the plug unit A can be loosely attached onto the socket unit B. The pin-shaped body 48 is retracted into the receptacle 43 so that the latching elements 35 with the latching lugs 36 of the attachment piece 34 can snap into the receptacle 43 with the recesses 45.

Figure 5:
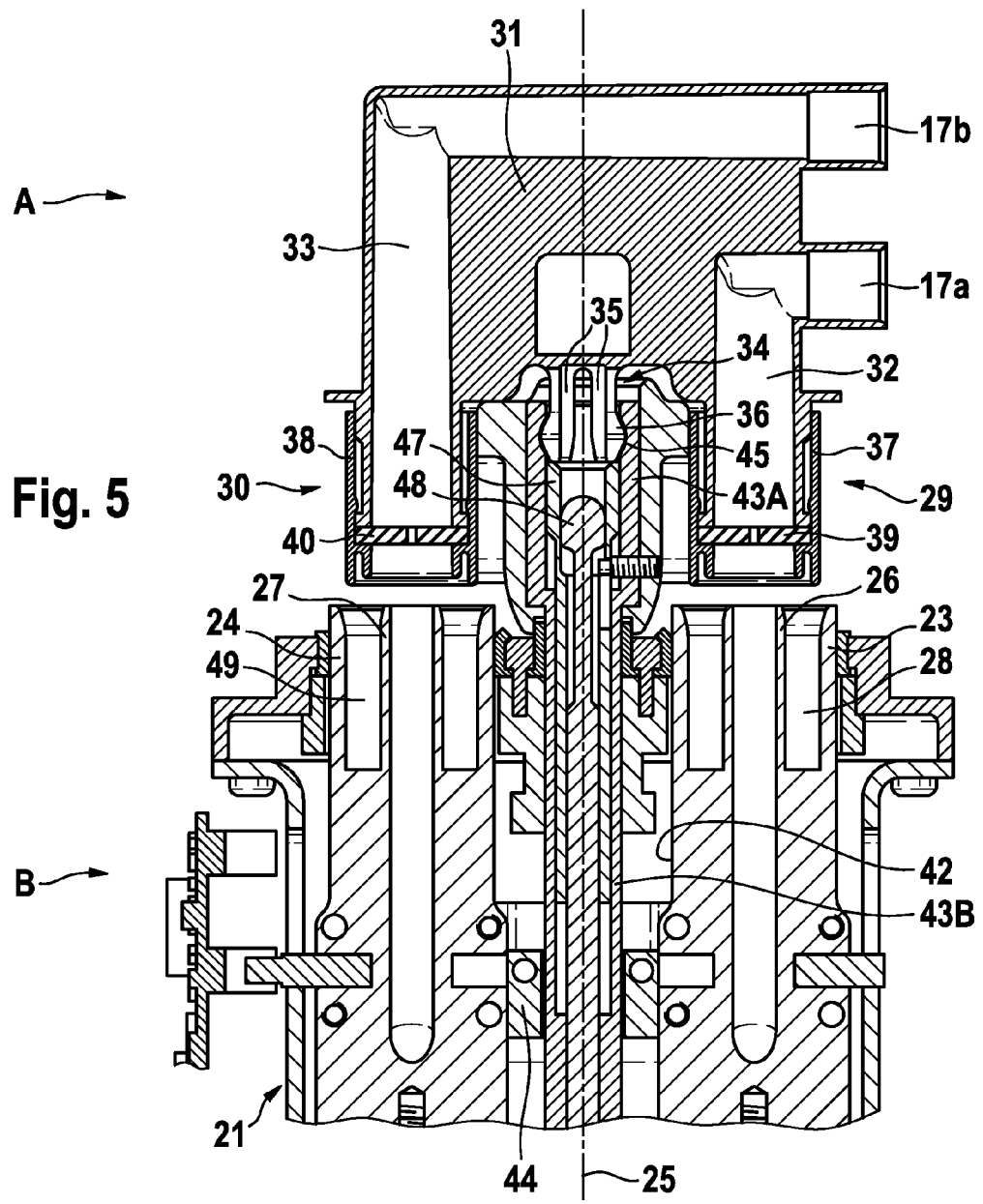
FIG. 5 shows a section through the plug unit and the socket unit of FIG. 2, wherein the plug unit is loosely inserted in the socket unit.
Figure 6:
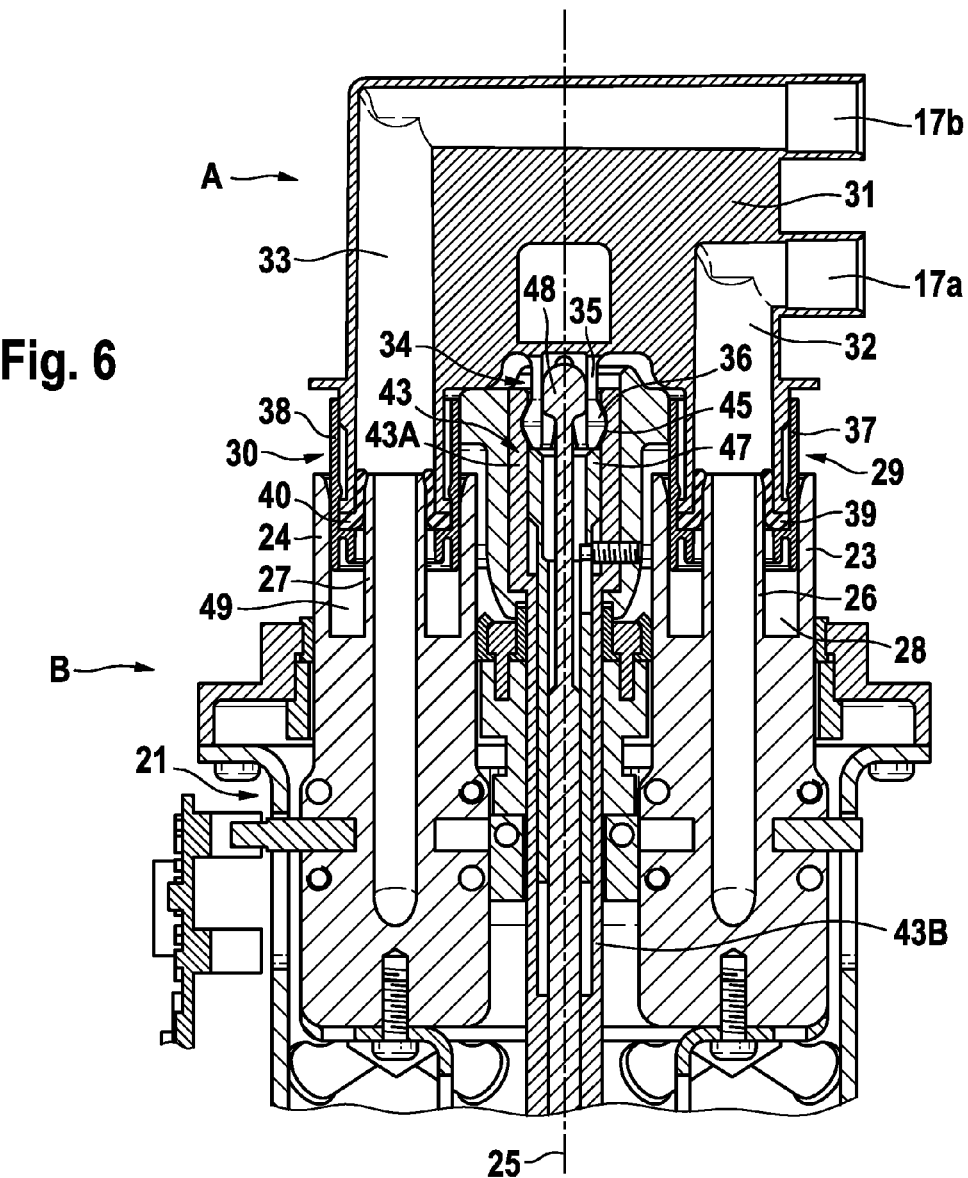
FIG. 6 shows a section through the plug unit and the socket unit of FIG. 2, wherein the plug unit is connected to the socket unit so that the flow connections are established.

FIG. 5 shows the position in which the plug unit A is loosely attached onto the socket unit B, wherein the attachment piece 34 is snapped into receptacle 43. Here, the plug unit A is only loosely held without the flow connections being established.

The position of the probing element 47 is monitored by a system (not shown in the Figures). Since the probing element 47 is pushed back by the attachment piece 34, it is detected that the plug unit A is loosely attached. When the plug unit is loosely attached, the drive unit is set in operation, whereby the pin-shaped body 48 in the receptacle 43 is pushed forward. Through this, the initially only loose connection between the attachment piece 34 and the receptacle 43 is locked. At the same time, the connecting parts 23, 24 with the connecting pieces 26, 27 are pushed forward out of the housing body 21.

By displacing the connecting parts 23, 24, the connecting pieces 26, 27 penetrate through the membranes 39, 40 of the plug unit A, whereby the fluid-tight connections between the connecting pieces and the connectors are established. Since after the interlocking of the attachment piece with the receptacle, the plug unit A is firmly attached on the socket unit B, the forces occurring when connecting the plug and socket units can be absorbed.

Detaching the plug unit A from the socket unit B is carried out in reverse order. For this, the pin-shaped body 48 in the receptacle 43 and the connecting parts 23, 24 with the connecting pieces 26, 27 in the housing body 21 are retracted, whereby the connection between the attachment piece 34 and the receptacle 43 is unlocked, and the connecting pieces 26, 27 are pulled out of the connectors 29, 30. Unlocking can take place simultaneously with retracting the connecting pieces or prior to retracting the connecting pieces.

The socket unit B comprises a closure body 50 for closing the two connecting parts 23, 24 so as to be able to carry out a rinsing process with a rinsing solution.

The closure body 50 has two closure pieces 51, 52 that are arranged at the same distance as the connectors 29, 30 of the plug unit A and have the same formation as the connectors of the plug unit. The two closure pieces 51, 52 are closed in the closure body 50 at their rear ends. On the two opposite sides on which the connectors 29, 30 are not arranged, the closure body 50 has semicircular cut-outs 53, 54. The cut-outs 53, 54 enclose with the closure pieces in each case a right angle.

The closure body 50 with the closure pieces 51, 52 is connected to the front section 43A of the receptacle 43 of the socket unit B. Since the receptacle 43 is mounted to be pivotable about the longitudinal axis 25, it is possible that by pivoting the receptacle 43 with the drive unit (not shown in the Figures), the closure body 50 with the closure pieces 51, 52 can also be pivoted about the axis 25.

FIG. 2 shows the closure body 50 with the closure pieces 51, 52 in the position in which the plug unit A can be attached onto the socket unit B. In this position, the semi-circular cut-outs 53, 54 are positioned in front of the connecting parts 23, 24 and/or connecting pieces 26, 27 of the socket unit B while the closure pieces 51, 52 are arranged in a plane that is perpendicular to the plane in which the connecting parts 23, 24 are arranged. In this position, the plug unit A can be plugged into the socket unit B.

For initiating the rinsing process, the closure body 50 with the connectors is swiveled by 90° by the drive unit (not shown in the Figures) by pivoting the receptacle 43 so that the closure pieces 51, 52 are positioned in front of the connecting parts 23, 24. However, the connecting pieces are not yet closed. Subsequently, the connecting parts 23, 24 are advanced out of the housing body 21 so that the closure pieces 51, 52 are slid into the connecting parts 23, 24. Thus, the rinsing chambers 28, 49 are closed in a fluid-tight manner (FIG. 3, FIG. 7). For sealing the closure pieces 51, 52 with respect to the connecting parts 23, 24, ring seals 55 can be provided. After the rinsing process is completed, the connecting parts are retracted again. The closure body with the closure pieces can now be pivoted back again into the initial position (FIG. 2).

It is an advantage that after aligning the closure pieces relative to the connecting parts through the relative movement of the closure pieces and the connecting parts, both parts engage with each other so that a fluid-tight closure of the rinsing chambers is ensured.

The socket unit B allows a fully automatic control of the connection of the plug unit A to the socket unit B and also of the initiation of the rinsing process so that the handling as a whole is simplified. Controlling is carried out with a central control unit that interacts with the position detection mechanism according to the present invention, wherein the position detection mechanism in this exemplary embodiment detects the linear position of the connecting parts 23, 24 and the pivot position of the tubular receptacle 43, which hereinafter are designated as drive body of the drive unit of the socket unit.

The position detection mechanism for detecting the linear position and/or angular position of one of the drive bodies of the drive unit of the medical device is described hereinafter in general terms with reference to FIGS. 8 to 12.

Figure 8:
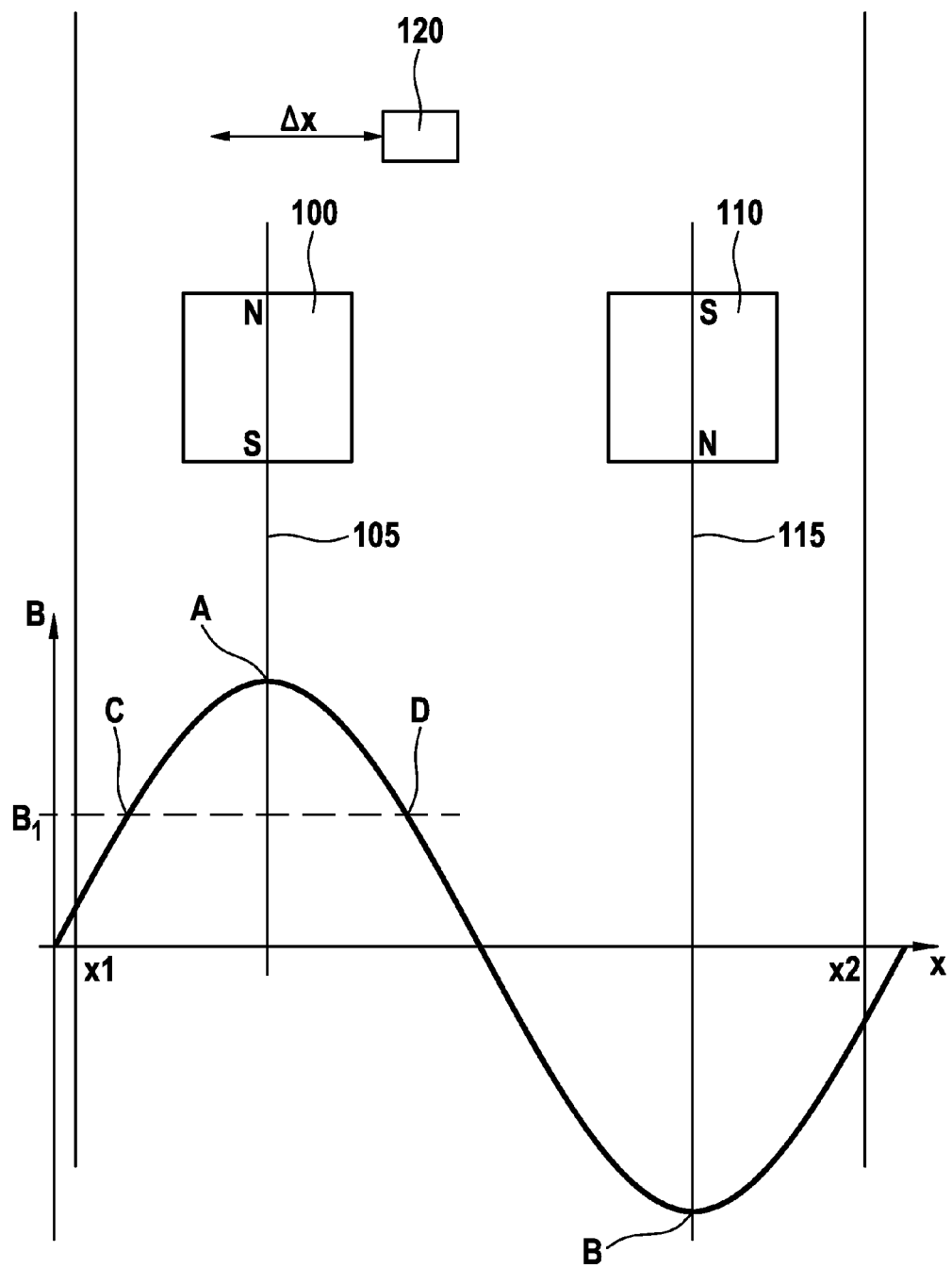
FIG. 8 shows an illustration of the magnetic field in an arrangement with two magnet elements and a sensor element for detecting the linear position.

FIG. 8 shows in a schematic illustration an arrangement of two magnet elements 100, 110 and a sensor element 120. The magnet elements 100, 110 are preferably permanent magnets that are arranged, for example, on a longitudinally displaceable drive body (not shown in the Figures), the linear position of which is to be detected. The sensor element 120 is preferably a Hall sensor that is stationarily arranged on a housing part (not shown in the Figures). The magnet elements 100, 110 are arranged spaced apart from each other in such a manner that their poles N and S face in opposite directions. It is assumed that the magnet elements 100, 110 that are arranged spaced apart from the sensor element 120 can be displaced by the distance Δx along an axis extending parallel to the magnets. However, the magnet elements 100, 110 can also be arranged stationarily on a housing part (not shown in the Figures), whereas the sensor element 120 is arranged on a longitudinally displaceable drive body (not shown in the Figures), the linear position of which is to be detected.

The sensor 120 generates an electrical signal that correlates with the magnetic flux density B. It can be seen that the absolute value of the magnetic flux density B at the height of the axis 105, 115 extending through north and south poles N, S of the magnets 100, 110 is a maximum and a minimum, respectively, and decreases toward both sides (positions A and B). This results in a sinusoidal curve. Furthermore, it can be seen that, for example in the positions C and D or all other positions on both sides of the symmetry axis, the magnetic flux density has the same absolute value although the sensor is located in different positions, i.e., viewed in the direction of the x-axis, the sensor lies before or behind the first magnet 100. A clear determination of the linear position of the sensor or the drive body is therefore not possible with the present measurement arrangement. The same result is obtained if a rotational movement of the drive body is detected with a comparable measurement arrangement.

FIGS. 9 and 10 show a first embodiment of the position detection mechanism with which the linear position of a drive body of the drive unit of the socket unit is detected.

The position detection mechanism comprises two magnet elements 100, 110, in particular permanent magnets, which are arranged spaced apart from each other on the longitudinally displaceable drive body 150, in particular the longitudinally displaceable connecting parts 23, 24 (FIG. 4), wherein the poles N, S of the magnets 100, 110 face in opposite directions. On a housing part 160 of the socket unit, two sensor elements 120, 130, in particular Hall sensors, are arranged opposite to the magnets and spaced apart from each other. The Hall sensors 120, 130 generate an electrical signal that correlates with the magnetic flux density. Moreover, the position detection mechanism can comprise an evaluation unit 180 that is connected via a data line to a control unit 190 through which the actuators (not shown in the Figures) of the drive unit of the socket unit are controlled. The evaluation unit 180 receives the electrical signals of the Hall sensors 120, 130 via signal lines 121, 131. The evaluation unit 180 can generate a first control signal for the control unit when the drive body 150 is in the advanced position (FIG. 10), and a second control signal when the drive body is in the retracted position (FIG. 9).

The evaluation unit 180, which can be a microprocessor, on which a data processing program (software) runs is configured such that based on the amplitude of the signal of the first Hall sensor 120, the two possible linear positions of the drive body 150 in relation to the symmetry axis 105 and 115, respectively, of the magnet is determined. Based on the sign of the signal of the second Hall sensor 130, the evaluation unit 180 determines if the linear position determined with the first sensor 120, when viewed in the direction of the X-axis, lies before or behind the symmetry axis 105 and 115, respectively. For example, if the sign of the signal of the second sensor 130 is positive, it is assumed that the first sensor 120 is situated before the symmetry axis and the drive body 150 is situated in the advanced position (FIG. 10), and in the case of a negative sign, it is assumed that the first sensor 120 is situated behind the symmetry axis 105 and the drive body 150 is situated in the retracted position (FIG. 9). The two magnets 120, 130 can also be arranged on the movable drive body 150, and the two sensors can be arranged on the stationary housing part 160.

The control unit 190 can provide continuous position detection for electrically controlling the actuators, wherein through processing the control signals of the evaluation unit 180, a clear position determination is possible. Dividing into an evaluation unit and a control unit shall serve only for illustrating the present invention. However, in practice, the control unit and the evaluation unit will be a common unit that is formed by a microcontroller.

For detecting the angular position of the drive body of the drive unit, the position detection mechanism can comprise two magnet elements and two sensor elements that are arranged on the drive body and/or housing part in a plane perpendicular to the axis of the drive body. Evaluating the signals for determining the angular position of the drive body takes place analogously to the signal evaluation for determining the linear position.

Figure 11:
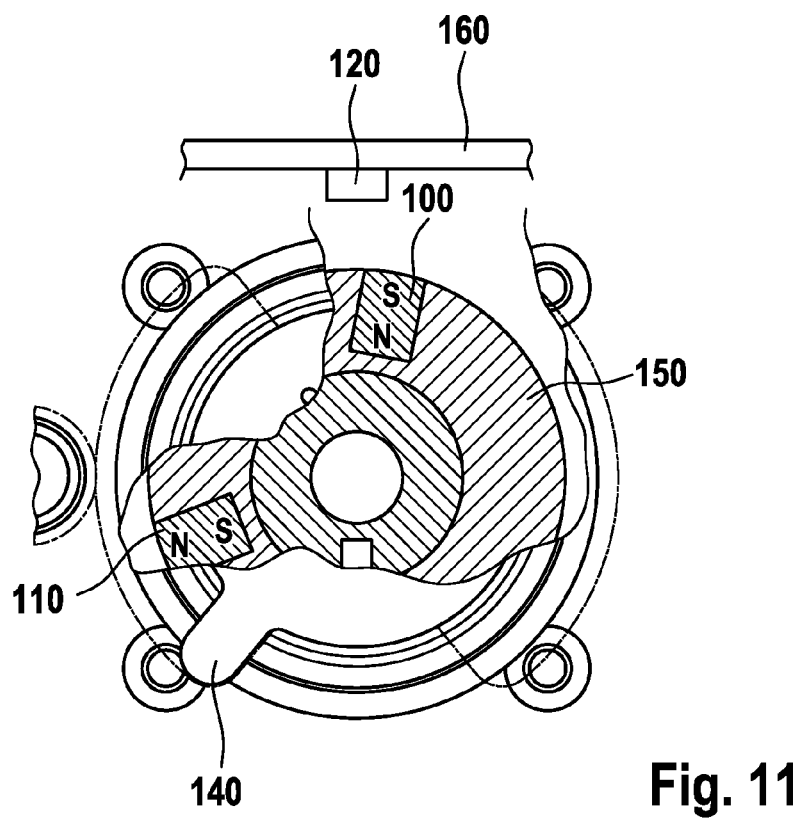
FIG. 11 shows a simplified illustration of an embodiment of the position detection mechanism with two magnet elements and a sensor element for detecting the angular position of a rotational drive body, wherein the drive body is in a first position.
Figure 12:
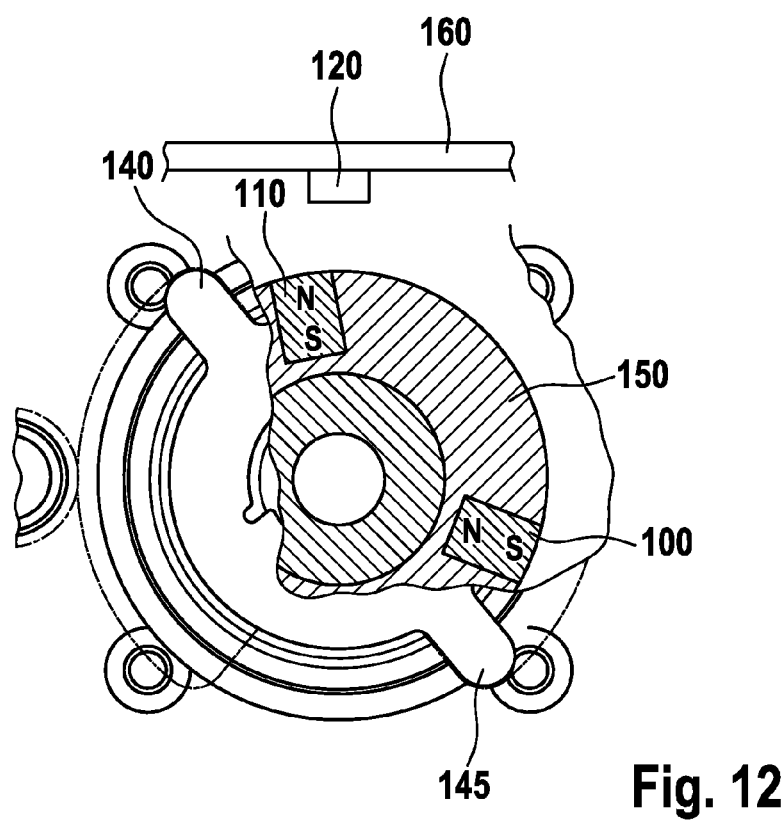
FIG. 12 shows the position detection mechanism of FIG. 11, wherein the drive body is in a second position.

FIGS. 11 and 12 show in a partial sectional illustration an alternative embodiment of the position detection mechanism that serves for determining the angular position of the drive body. This mechanism differs from the position detection mechanism of FIGS. 9 and 10 in that it comprises only one sensor element 120 that is fastened to the housing part 160. The parts corresponding to each other are indicated again with the same reference numbers.

The evaluation unit that is not illustrated in FIGS. 11 and 12 is configured such that based on the amplitude of the signal of the only Hall sensor 120, the two possible angular positions of the drive body 150 in relation to the symmetry axis of the magnet shown in FIG. 8 is determined, i.e., an angular position before and/or behind the symmetry axis. Furthermore, the evaluation unit determines the sign of the gradient of the magnetic field detected by the only Hall sensor in the case of a change of the angular position and determines based on the sign of the gradient whether the angular position determined with the first Hall sensor 120 lies before or behind the symmetry axis.

FIG. 8 shows for the analogous case of a translational movement of the sensor that the angular position is clearly defined through the sign of the gradient. Assume that $B_1$ is the amplitude of the measurement signal for the positions C and D. However, through this, the position is not clearly defined. For example, if the gradient of the magnetic flux density is negative, i.e., the slope of the sinusoidal curve is negative, it is assumed that the sensor is in the position D so that the evaluation unit generates the first control signal, whereas in the case of a positive gradient, i.e., the slope of the curve is positive, it is assumed that the sensor is in the position C so that the evaluation unit generates the second control signal.

For determining the sign of the gradient, a change of the angular position and/or the linear position by just a small amount is sufficient. Determining the sign of the gradient, i.e., an increase or decrease of the magnetic flux density, therefore can take place only for the actual measurement. However, it is also possible to determine the sign of the gradient if the drive body has to be displaced or pivoted anyway.

Another alternative embodiment with only one sensor element 120 provides to predefine a measuring range in which a clear determination of the position is possible. This measuring range is the range which in FIG. 8 lies between the two symmetry axes 105, 115. Thus, in the alternative embodiment, two end stops are provided which limit the movement range of the drive body 150 in both directions. These end stops 140, 145 are illustrated in FIGS. 11 and 12 only in outlines. FIG. 11 shows the angular position in which the drive body 150 abuts against the one end stop, and FIG. 12 shows the angular position in which the drive body abuts against the other end stop. The pivot angle is dimensioned here such that the magnets 100, 110 cannot move beyond the symmetry axes into positions in which the angular position of the drive body cannot be clearly determined with a single sensor.

The position detection mechanism according to the present invention represents a simple but reliable measuring system by means of which controlling the medical device can be improved. Controlling the device can be carried out with the control unit 190 based on the control signals of the evaluation unit 180.

The clear determination of the position with two or more sensor elements outside of a measuring range that does not permit a clear determination with only one sensor element allows an arrangement of the individual elements in which a high resolution and a high measuring accuracy can be achieved.

What is claimed is:

1. A medical device, comprising:
   a socket unit for connecting a plug unit of a device for providing medical fluids, wherein the socket unit includes at least one connecting piece for connecting at least one connector of the plug unit; and
   a connecting mechanism of the socket unit for establishing a connection between the at least one connecting piece and the at least one connector,
   wherein the at least one connecting piece is configured to connect to the at least one connector so that a flow connection for feeding fresh fluids or discharging used fluids can be established when connecting the at least one connector to the at least one connecting piece,
   wherein the connecting mechanism includes:
      a drive unit having at least one movable drive body for carrying out at least one of a translational or rotational movement; and
      at least one position detection mechanism for detecting at least one of the linear position or the angular position of the at least one movable drive body, wherein the position detection mechanism includes:
         at least two magnet elements arranged spaced apart from each other and which generate a magnetic field;
         at least one sensor element that detects the magnetic field of the at least two magnet elements; and
         an evaluation unit that is configured to determine at least one of the linear position or the angular position of the at least one movable drive body based on the magnetic field generated by the at least two magnet elements and detected by the at least one sensor element,
         wherein either (i) the at least two magnet elements are arranged on the at least one movable drive body and the at least one sensor element is arranged stationarily, or (ii) the at least two magnet elements are arranged stationarily and the at least one sensor elements is arranged on the at least one movable drive body.

2. The medical device according to claim 1, wherein the at least two magnet elements include a first magnet element and a second magnet element that are arranged spaced apart from each other with opposite polarity, and wherein the at least one sensor element includes a first sensor element and a second sensor element that are spaced apart from each other, and wherein the evaluation unit is configured to determine:
   based on the magnetic field detected by the first sensor element, at least one of two possible linear positions or two possible angular positions of the at least one movable drive body, and
   based on the magnetic field detected by the second sensor element, at least one of whether the at least one of the two possible linear positions is the first linear position or the second linear position or whether the at least one of the two angular positions is the first angular position or the second angular position.

3. The medical device according to claim 2, wherein the evaluation unit is configured to determine, based on the sign of the magnetic field detected by the second sensor element, at least one of whether the at least one of the two possible linear positions is the first linear position or the second linear position or whether the at least one of the two angular positions is the first angular position or the second angular position.

4. The medical device according to claim 1, wherein the translational movement of the at least one movable drive body is limited by one or a plurality of stop elements.

5. The medical device according to claim 1, wherein the rotational movement of the at least one movable drive body is limited by one or a plurality of stop elements.

6. The medical device according to claim 1, wherein the at least two magnet elements include a first magnet element and a second magnet element that are arranged spaced apart from each other with opposite polarity, and wherein the at least one sensor element includes a first sensor element, and wherein the evaluation unit is configured to determine:
   based on the magnetic field detected by the first sensor element, at least one of two possible linear positions or two possible angular positions of the at least one moveable drive body;
   if there is a change in at least one of the linear position or the angular position of the at least one moveable drive body, a gradient of a change of the magnetic field; and
   based on a sign of the gradient of the change, at least one of whether the at least one of the two possible linear positions is the first linear position or the second linear position or whether the at least one of the two angular positions is the first angular position or the second angular position.

7. The medical device according to claim 1, wherein the at least one moveable drive body includes means for detachably connecting the plug unit to the socket unit.

8. The medical device according to claim 7, wherein the means for detachably connecting the plug unit to the socket unit includes a receptacle for plugging in an attachment piece of the plug unit.

9. The medical device according to claim 1, wherein the evaluation unit generates:
   a first control signal when the position detection mechanism detects a first advanced position of the at least one moveable drive body in which the at least one connector and the at least one connecting piece are disconnected; and
   a second control signal when the position detection mechanism detects a second retracted position of the at least one moveable drive body in which the at least one connector is connected to the at least one connecting piece.

10. The medical device according claim 1, wherein the at least one moveable drive body is pivotable about a pivot axis.

11. The medical device according to claim 10, wherein:
    the at least one connecting piece is concentrically enclosed by a connecting part to form a rinsing chamber;
    the socket unit has a closure body with at least one closure piece for closing the at least one rinsing chamber;
    the closure body is provided on the pivotable drive body, and the at least one closure piece is arranged on the closure body and is spaced apart from the pivot axis;
    in a first pivot position, the at least one closure piece and the at least one connecting part lie on a common axis so that through a relative movement of the plug unit and the socket unit, a connection between the closure piece and the connecting piece can be established for closing the rinsing chamber; and
    in a second pivot position, the at least one closure piece and the at least one connecting piece are arranged offset to each other so that when plugging the plug unit into the socket, a connection between the at least one connector of the plug unit and the at least one connecting piece of the socket unit can be established.

12. The medical device according to claim 11, wherein the evaluation unit generates:
  a first control signal when the position detection mechanism detects the first pivot position; and
  a second control signal when the position detection mechanism detects the second pivot position.

13. The medical device according to claim 1, wherein the at least two magnet elements are permanent magnets.

14. The medical device according to claim 1, wherein the sensor element is a Hall sensor.

15. The medical device according to claim 1, wherein the medical device is a blood treatment device.

16. The medical device according to claim 15, wherein the blood treatment device is an extra-corporal dialysis device or a device for peritoneal dialysis.

\* \* \* \* \*